United States Patent [19]
Bidwell

[11] Patent Number: 5,053,042
[45] Date of Patent: Oct. 1, 1991

[54] BIOPSY NEEDLE GUIDE FOR USE WITH CT SCANNER

[76] Inventor: Clifford D. Bidwell, 1395 Doliver Dr., Orlando, Fla. 32803

[21] Appl. No.: 465,915

[22] Filed: Jan. 16, 1990

[51] Int. Cl.$^5$ ............................................. A61B 10/00
[52] U.S. Cl. ...................................... 606/130; 33/512; 378/208
[58] Field of Search .................. 606/130; 33/512, 534, 33/514.1; 128/774, 662.05; 378/205, 208, 209

[56] References Cited

U.S. PATENT DOCUMENTS

| | | | |
|---|---|---|---|
| 2,430,133 | 7/1957 | Thompson | 33/512 |
| 4,465,064 | 8/1984 | Barbier et al. | 606/130 |
| 4,706,665 | 11/1987 | Gouda | 606/130 |

FOREIGN PATENT DOCUMENTS

| | | | |
|---|---|---|---|
| 2115121 | 10/1972 | Fed. Rep. of Germany | 606/130 |
| 2139433 | 2/1973 | Fed. Rep. of Germany | 606/130 |
| 3339259 | 3/1985 | Fed. Rep. of Germany | 606/130 |
| 0602052 | 7/1978 | Switzerland | 33/512 |

Primary Examiner—Lee S. Cohen
Assistant Examiner—Scott R. Akers
Attorney, Agent, or Firm—William M. Hobby, III

[57] ABSTRACT

A planar template and measuring device is provided for guiding a biopsy needle to a predetermined point with angular and radial coordinates, in a cross-sectional plane of a patient's torso, derived from CT scans of the patient. The device is configured to fit across and around the torso of a patient lying on the table of a CT scanner, when the device is positioned at right angles to the plane of the table and the long axis of the patient. The template is slidably mounted on rails attached to the long sides of the table so that it can be positioned at any point on the long axis of the patient. The device has an arcuate slot defining a part-circle marked with an angular scale, the center of which coincides with a central reference point of the CT scanner. A sliding carriage for a biopsy needle travels along the slot and may be set at any desired angle relative to the part-circle. The carriage has brackets which hold the needle in radial alignment relative to the part-circle and parallel to a linear scale scribed on the carriage. One of the brackets is adjustable permitting the needle to be set at any desired position along a given radius.

3 Claims, 2 Drawing Sheets

BIOPSY NEEDLE GUIDE FOR USE WITH CT SCANNER

BACKGROUND OF THE INVENTION

I. Field of the Invention

The present invention relates to medical diagnostic techniques including computed tomography scanning of a patient, and more particularly to a device for guiding a biopsy needle to an exact location based on information obtained by computed tomography scanning.

II. Prior art

A number of devices currently exist for making physical measurements of a patient's body or parts thereof. U.S. Pat. No. 4,135,498 issued to McGee includes a non-opaque viewing screen with a vertical scale, a measuring bar with slides along the vertical scale, and an angle measuring arm and angular scale. The patient stands behind the screen, and X-rays are aligned on the screen relative to the patient and illuminated. Measurements of the patient in relation to the X-rays may thus be made.

U.S. Pat. No. 4,440,168 to Warren is for a surgical device for marking angles and positions on bones or other body tissue with respect to a reference point, in preparation for surgery.

U.S. Pat. No. 4,630,375 to Spolyar is for a template-like gauge having a reference point and linear and angular scales relative to the reference point. The gauge is used in connection with a standardized lateral cephalogram of a patient to precisely determine spatial coordinates for focusing an X-ray source in obtaining a radiograph of the patient's temporo-mandibular joint.

U.S. Pat. No. 4,279,259 to Lee discloses a mammometer for making various breast-related measurements, including location, shape, size, necessary for various kinds of breast surgeries.

It has long been possible to focus sources of radiation, including X-rays and laser beams, at an exact location within the human body. The development of computed tomography scanners has made possible the determination of spatial coordinates of a diseased or problem area within the body. However there are no known devices for guiding a biopsy needle to a precise location within the body.

Accordingly it is an object of this invention to provide a biopsy needle guide for use in connection with a computed tomography scanner, which can measure and control the angle and depth of penetration of a biopsy needle in a given cross-sectional plane of a patient's body, so that the physician may insert the biopsy needle to the precise location determined from the tomagrams.

SUMMARY OF THE INVENTION

According to the present invention, a planar template and measuring device is provided for guiding a biopsy needle to a predetermined point defined by its angular and radial coordinates in a cross-sectional plane of a patient, derived from CT scans of the patient. The template is slidably mounted on rails attached to the long sides of the table so that it can be positioned at any point on the long axis of the patient. The device has an arcuate slot defining a reference part-circle marked with an angular scale. A sliding carriage for a biopsy needle travels along the slot and may be set at any desired angle relative to the part-circle. The carriage has brackets which hold the needle in radial alignment relative to the part-circle and parallel to a linear scale scribed on the carriage, permitting the needle to be set at any desired penetration along a given radius. The device is configured to fit across and around the torso of a patient lying on the table of a CT scanner, when positioned at right angles to the plane of the table and the long axis of the patient, with the center point of the reference part-circle coinciding with the center reference point of the CT scanner.

BRIEF DESCRIPTION OF THE DRAWINGS

A better understanding of the present invention may be obtained upon reference to the drawings together with the following detailed description thereof, wherein like reference characters refer to like parts throughout the several views.

DETAILED DESCRIPTION OF THE PREFERRED EMBODIMENT

Figure 1:
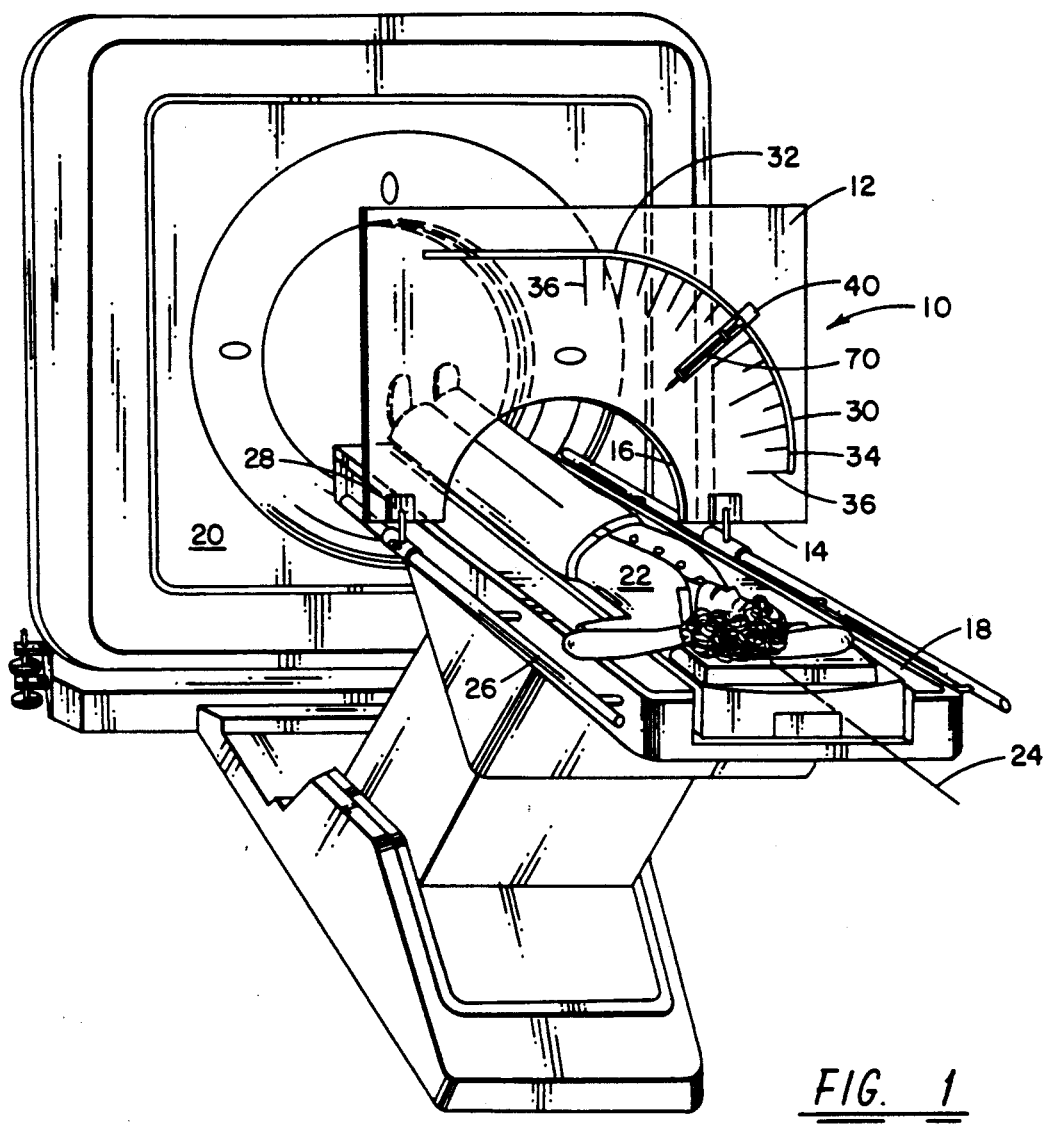
FIG. 1 is a perspective view of the device in position for use, together with a biopsy needle, CT scanner and table with a patient lying thereon.
Figure 3:
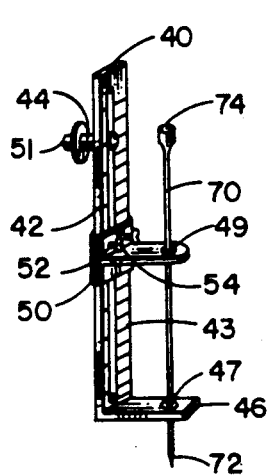
FIG. 3 is a perspective view of the needle carriage with linear scale and needle brackets.
Figure 4:
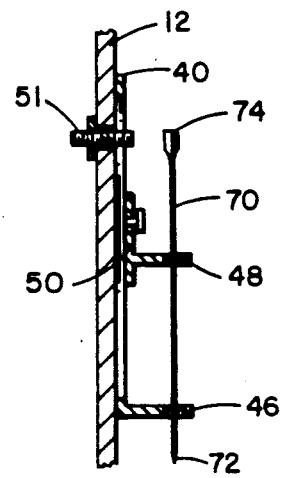
FIG. 4 is a longitudinal section of the needle carriage.
Figure 2:
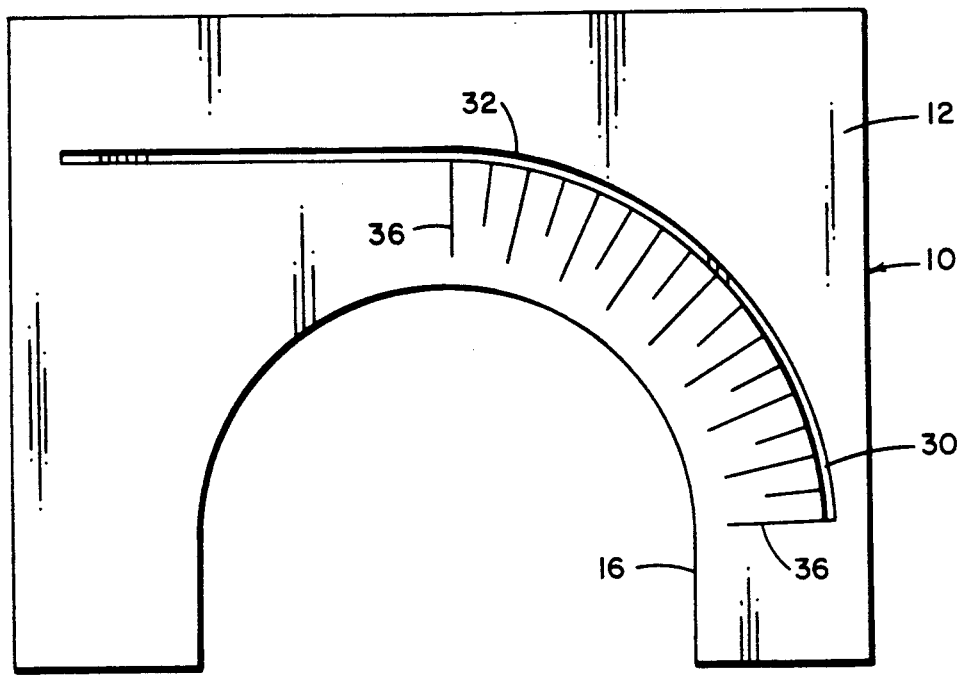
FIG. 2 is a relatively enlarged planar view of the device depicting the arcuate slot and angular scale.
Figure 5:
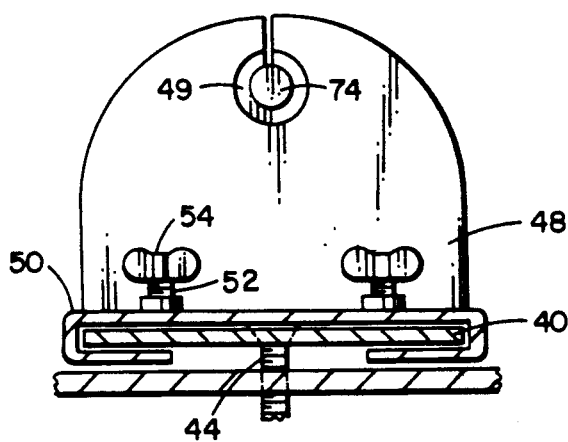
FIG. 5 is a cross-sectional view of one embodiment of a sliding bracket member.
Figure 6:
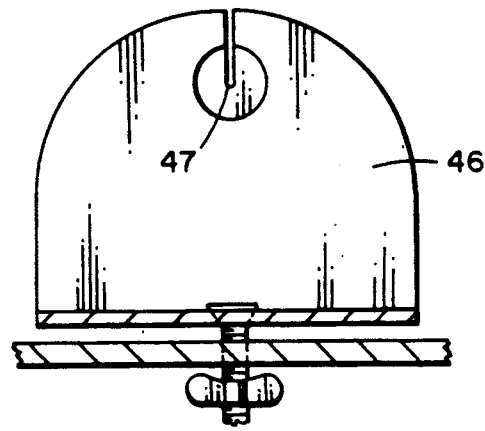
FIG. 6 is a cross-sectional view of one embodiment of a fixed bracket member.

With reference to the drawings, a preferred embodiment of the biopsy needle guide according to the present invention is hereinafter described. As seen in FIGS. 1-2, the device 10 comprises a planar member 12 which is preferably of a transparent or translucent material such as lucite. Transparency of the material permits reversing the apparatus 10, the utility of which will be apparent from the ensuing description. The overall shape of the perimeter of the planar member is not critical except for one edge 14 of the device which should be straight at each end thereof, with a hollowed-out area 16 in the middle portion thereof to allow alignment of edge 14 at either end with the plane of the table 18 of a CT scanner 20, while fitting around and across the torso 22 of a patient lying on table 18 of the scanner 18. The CT scanner 20 and table 18 shown in FIG. 1 are a simplified representation of a General Electric instrument, "CT Pace". More information on the operation of this machine and the images produced thereby is obtainable in a brochure published by GE Medical Systems, P. O. Box 414, Milwaukee, Wis. 53201.

Perforating the planar member 12 is an arcuate slot 30 on which is mounted a needle carriage 40 holding a biopsy needle 70. The slot 30 preferably defines a reference part-circle comprising at least 90° from a point 32 directly above the central line 24 of the patient 24 to the horizontal axis 34 of the reference part-circle. The device is configured for positioning so that the center of the reference part-circle will coincide with the center of a cross-sectional plane of the patient's torso 22 as depicted or indexed in the tomography images produced by the scanner 20.

Planar member 12 should be mounted on table 18 so that any position relative to the long axis 24 of the patient can be selected. There are numerous conventional ways in which the position of planar member 12 could be varied. FIG. 1 depicts a pair of rails 26 attached to the table 18, one on each of the long sides, and a pair of clamps 28, one slidably mounted on each of the rails 26. Planar member 12 is held securely by the clamps which are used to slide planar member 12 back or forth to position the biopsy needle in the desired cross-sectional plane of the patient's torso 22.

An angular scale 36 through 90° of a circle is shown scribed on the inner circumference of slot 30. Using transparent or translucent material for the planar member 12 permits the device 10 to be reversed so that the quarter-circular slot and scale can be placed over either the right or left side of table 18, with full visibility of the scale 36 and needle 70 to the physician-operator from the same vantage point. Alternatively the arcuate slot 30 and scale 34 could extend a full 180° all the way from one side of table 18 and patient 22 to the other.

Needle carriage member 40 has preferably a flat elongate strip 42 of metal or stiff plastic on which is scribed a linear scale 43. A locking assembly 44 has a nut and bolt 51 attached through an elongated slot in strip 42 and is used to hold the strip 42 in radial alignment relative to the reference part-circle, at any desired angular position along the slot 30.

A fixed bracket member 46 is mounted at one end of strip 42. Bracket member 46 is located at the proximal end relative to the center of the reference part-circle, and has a bore 47 sized to hold a standard biopsy needle 70 in snug sliding engagement. A movable bracket member 48 has a similar bore 49 and a locking assembly 50, whereby bracket member 48 may be releasably fixed at any desired point along scale 43. Locking assembly 50 may consist simply of a bolt 52 and cooperating wing nut 54 arrangement, although any other suitable releasable locking system could be substituted therefor.

To operate the biopsy needle guide 10, the planar member 12 is positioned in the desired cross-sectional plane of the patient's torso 22 by sliding the clamps 28 along the side rails 26 attached to table 18 until the desired position is attained. A biopsy needle 70 is inserted through bores 47 and 49 in brackets 46 and 48 so that the pointed end 72 of needle 70 is closest to the patient. The opposite end 74 of the needle is too large to pass through the bore 49 and operates as a stop so that the position of the point 72 along a given radius, corresponding to a radial coordinate determined from a tomagram cross-sectional image, can be accurately controlled and adjusted by adjusting the position of sliding bracket member 48 along scale 43. Similarly, the carriage member 40 may be set and locked at any desired angular position along slot 30 corresponding to an angular coordinate taken from the CT scan images. The biopsy needle tip 72 can thus be positioned to reach any point within a quadrant of a circle defined by the cross-sectional plane of the patient's torso 22 coinciding with the plane of the invention 12, and the radial lines extending from the center line 24 of the patient to points 32 and 34. It should be obvious to anyone skilled in the art that the other three quadrants of the cross-sectional plane can be reached by either having the patient turn over on the table or reversing the device 10, or a combination of both.

Although only a preferred embodiment of the invention has been disclosed and described it is apparent that other embodiments and modifications of the invention as well as dimensional relationships therein and thereof are possible within the scope of the appended claims.

I claim:

1. A guide for a biopsy needle designed for use in connection with a CT scanner comprising:
    a computer tomography scanning device table;
    a planar member, one edge of said planar member lying on said table when said planar member is at right angles to the plane of the table and the long axis of the patient, said planar member being perforated with an arcuate slot defining reference part-circle disposed so that the center of said reference part-circle will coincide with the center reference point of images produced by a scanning device when said planar member is positioned for use and said planar member having an angular scale of radial lines adjacent said slot;
    adjustable means for mounting said planar member on said table, said means allowing said planar member to be positioned in any cross-sectional plane of the patient, said adjustable mounting means comprising a pair of rails, one rail attached to each side of the table parallel to the long axis of the patient, and a pair of clamps for holding the planar member, one clamp slidably mounted on each of said rails;
    an elongate sliding carriage member for holding a biopsy needle parallel thereto, said carriage member being mounted in radial alignment relative to said reference part-circle, for curvilinear travel along said arcuate slot;
    adjustable needle bracket means mounted on said carriage member for holding said biopsy needle in strict radial alignment relative to said reference part-circle, and for adjusting the radial penetration of said biopsy needle relative to said reference part-circle; and
    linear scale means scribed the length of said carriage member for measuring radial position of said biopsy needle relative to said reference part-circle.

2. The device according to claim 1 wherein said carriage member has an inner end and an outer end relative to the center of said reference part-circle and a lengthwise slot extending almost to each end, and said adjustable needle bracket means comprises a fixed bracket member and a sliding bracket member, the fixed bracket member being positioned at the inner end of said carriage member and having a bore permitting snug sliding movement of a biopsy needle therethrough, and the sliding bracket member mounted for linear travel along said lengthwise slot between said fixed bracket member and said outer end, said sliding bracket member having a bore permitting non-sliding releasable engagement of the handle portion of a biopsy needle, said bracket members cooperating to permit positioning of a biopsy needle held thereby at varying points along said lengthwise slot while maintaining parallel alignment of said needle with said carriage member and with a radius of said reference part-circle.

3. The device according to claim 2 further comprising a first locking means for releasably securing said carriage member at any point along said arcuate slot, and a second locking means for releasably securing said sliding bracket member at any point along said lengthwise slot.

* * * * *